United States Patent
Jung

(10) Patent No.: US 9,249,312 B2
(45) Date of Patent: Feb. 2, 2016

(54) ECO-FRIENDLY WATER-BASED PAINT COMPOSITION FOR INTERIOR FINISHING MATERIALS OF BUILDINGS

(71) Applicant: Hyeok Jung Kim, Cheonan-si, Chungcheongnam-do (KR)

(72) Inventor: Min Sang Jung, Cheonan-si (KR)

(73) Assignee: Hyeok Jung Kim, Chungcheongnam-Do (KR)

( * ) Notice: Subject to any disclaimer, the term of this patent is extended or adjusted under 35 U.S.C. 154(b) by 0 days.

(21) Appl. No.: 14/348,745

(22) PCT Filed: Jun. 12, 2013

(86) PCT No.: PCT/KR2013/005155
§ 371 (c)(1),
(2) Date: Mar. 31, 2014

(87) PCT Pub. No.: WO2014/104498
PCT Pub. Date: Jul. 3, 2014

(65) Prior Publication Data
US 2015/0337142 A1 Nov. 26, 2015

(30) Foreign Application Priority Data
Dec. 26, 2012 (KR) .................. 10-2012-0152939

(51) Int. Cl.
| | |
|---|---|
| C09D 1/00 | (2006.01) |
| C09D 7/12 | (2006.01) |
| C09D 5/14 | (2006.01) |
| C08K 3/36 | (2006.01) |
| C08K 3/22 | (2006.01) |

(52) U.S. Cl.
CPC ... *C09D 5/14* (2013.01); *C08K 3/22* (2013.01); *C08K 3/36* (2013.01); *C08K 2003/2227* (2013.01); *C08K 2003/2241* (2013.01); *C08K 2003/2265* (2013.01)

(58) Field of Classification Search
CPC .......... C09D 1/00; C09D 5/00; C09D 7/1291; C09D 5/14; A01N 25/28
USPC ........................................ 106/15.05
See application file for complete search history.

(56) References Cited

FOREIGN PATENT DOCUMENTS

| | | | |
|---|---|---|---|
| JP | 2002-167524 A | * | 6/2002 |
| KR | 1020000007111 | | 2/2000 |
| KR | 1020050038358 | | 4/2004 |
| KR | 1020050111443 | | 11/2005 |
| KR | 1020060099703 | | 9/2006 |
| KR | 10-2008-0009585 | * | 1/2008 |
| KR | 10-874126 B1 | * | 12/2008 |
| KR | 10-2009-0020105 A | * | 2/2009 |
| KR | 10-2009-0047983 A | * | 5/2009 |
| KR | 10-2010-0041250 A | * | 4/2010 |
| KR | 1020100074829 | | 8/2010 |
| KR | 1020100095178 | | 8/2010 |
| KR | 1020120111090 | | 10/2012 |

* cited by examiner

*Primary Examiner* — Anthony J Green
(74) *Attorney, Agent, or Firm* — IPLA P.A.; James E. Bame

(57) ABSTRACT

Disclosed is an eco-friendly water-based paint composition for interior finishing materials of buildings. The eco-friendly water-based paint composition includes: 3 to 6 wt. % of diatomite for adsorbing harmful materials; 7 to 12 wt. % of titanium dioxide for enhancing a deodorization effect; 0.4 to 1.5 wt. % of antimicrobial agent-containing microcapsules for killing harmful microorganisms derived from an indoor air; 0.1 to 0.5 wt % of preservative for suppressing and preventing propagation of fungi derived from indoor air; 30 to 40 wt. % of an inorganic binder for binding different ingredients of the water-based paint composition so as to form a smooth surface; 3 to 10 wt. % of water for blending different materials for the water-based paint and controlling workability; and residual silica for forming thickness during painting as a base material of the water-based paint.

6 Claims, 14 Drawing Sheets

TEST REPORT

1. Test report No. : ESR2730024
2. Client
   - Company name : B&G Communication Co., Ltd.
   - Address : 45-1010 (Seocho Eovill, Seocho-dong), Hyoryeong road 53, Seocho-gu, Seoul, Korea
   - Referral date : July 30, 2012
   - Test report issue date : October 5, 2012
3. Use of the test report : Quality control
4. Sample name : Functional coating material
5. Test results --- See the attached pages ---

| Confirmation | Drafts man Name | Jang Gye-Sung | Technical director Name | Yoo Kyoung-Whan |
|---|---|---|---|---|

Note: 1. This test report is a result of testing with specimens wherein the specimens and the specimen names have been provided by the client, and it does not guarantee the quality of all the products.
2. This test report may not be used for promotion, propaganda, advertisement or litigation, and is prohibited to be used for any purpose other than the agreed upon use.

President of Korea Conformity Laboratories (Sealed)

Head laboratory : Gasan-dong 459-28, Geumcheon-gu, Seoul, 153-803 Korea
Contact the results : Safety & environment center (Hyundai I-Valley 805, Dang-dong 14-1, Gunpo-city, Gyeonggi-do, Korea) Tel: 031-389-9184

FIG. 1A

TEST REPORT

Test report No. : ESR2730024

| Test item | | Test result | | | Test method |
|---|---|---|---|---|---|
| | | Initial concentration (CFU/Ml) | Concentration after 24 hours, (CFU/Ml) | Microorganism reduction rate (%) | |
| Antimicrobial test by *Escherichia coli* | BLANK | $1.8 \times 10^4$ | $5.1 \times 10^4$ | - | KCL-FIR-1002 :2011 |
| | Functional wall coating material | $1.8 \times 10^4$ | <10 | 99.9 | |
| Antimicrobial test by *Pseudomonas aeruginosa* | BLANK | $1.9 \times 10^4$ | $5.4 \times 10^4$ | - | |
| | Functional wall coating material | $1.9 \times 10^4$ | <10 | 99.9 | |
| Antimicrobial test by *Staphylococcus aureus* | BLANK | $1.5 \times 10^4$ | $4.7 \times 10^4$ | - | |
| | Functional wall coating material | $1.5 \times 10^4$ | <10 | 99.9 | |

※ CFU: Colony Forming Unit

※ Organism concentration of inoculum strain (CFU/mL): *Escherichia coli* : $1.8 \times 10^4$, *Pseudomonas aeruginosa* : $1.9 \times 10^6$, *Staphylococcus aureus* : $1.5 \times 10^6$ ※ used strains : *Escherichia coli* ATCC 25922
　　　　　　　*Pseudomonas aeruginosa* ATCC 15442
　　　　　　　*Staphylococcus aureus* ATCC 6538

※ Sample : 4 g

TEST REPORT

1. Test report No. : ESR2730026
2. Client
   ○ Company name : B&G Communication Co., Ltd.
   ○ Address : 45-1010 (Seocho Eovill, Seocho-dong), Hyoryeong road 53, Seocho-gu, Seoul, Korea
   ○ Referral date : July 30, 2012
   ○ Test report issue date : October 5, 2012
3. Use of the test report : Quality control
4. Sample name : Functional coating material
5. Test results --- See the attached pages ---

| Confirmation | Drafts man Name | Jang Gye-Sung | Technical director Name | Yoo Kyoung-Whan |
|---|---|---|---|---|

Note: 1. This test report is a result of testing with specimens wherein the specimens and the specimen names have been provided by the client, and it does not guarantee the quality of all the products.
2. This test report may not be used for promotion, propaganda, advertisement or litigation, and is prohibited to be used for any purpose other than the agreed upon use.

President of Korea Conformity Laboratories (Sealed)

Head laboratory : Gasan-dong 459-28, Geumcheon-gu, Seoul, 153-803 Korea
Contact the results : Safety & environment center (Hyundai I-Valley 805, Dang-dong 14-1, Gunpo-city, Gyeonggi-do, Korea) Tel: 031-389-9184

FIG. 2A

TEST REPORT

Test report No. : ESR2730026

| Test item | Test result | | | | Test method |
|---|---|---|---|---|---|
| | Period of Incubation test | | | | |
| | After 1 week | After 2 weeks | After 3 weeks | After 4 weeks | |
| Anti-fungal test | 0 | 0 | 0 | 0 | ASTM G 21 :2009 |

※ Fungal strains (mixed fungal strain)
  *Aspergillus niger* ATCC 9642
  *Penicillium pinophilum* ATCC 11797
  *Chaetomium globosum* ATCC 6205
  *Gliocladium virens* ATCC 9645
  *Aureobasidium pullulans* ATCC 15233

※ Read of results
  0 : Mycelia growth at inoculated part of specimen are not identified.
  1 : Identified Mycelia growth range at inoculated part of specimen is less than 10% of total area.
  2: Identified Mycelia growth range at inoculated part of specimen is 10 to 30% of total area.
  3: Identified Mycelia growth range at inoculated part of specimen is 30 to 60% of total area.
  4: Identified Mycelia growth range at inoculated part of specimen is 60% or more of total area.

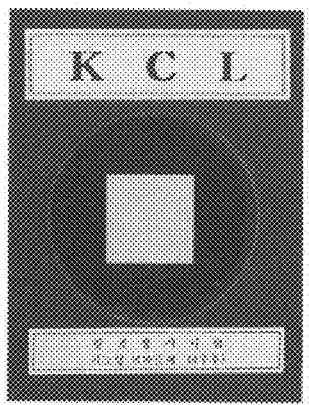

<Picture 1>
— Intentionally blank section below —

TEST REPORT

1. Test report No. : ESR2730031
2. Client
   ○ Company name : B&G Communication Co., Ltd.
   ○ Address : 45-1010 (Seocho Eovill, Seocho-dong), Hyoryeong road 53, Seocho-gu, Seoul, Korea
   ○ Referral date : July 30, 2012
   ○ Test report issue date : October 18, 2012
3. Use of the test report : Quality control
4. Sample name : Functional paint
5. Test results

| Test item | Unit | Class | Test result | Test method |
|---|---|---|---|---|
| Total volatile organic compounds (TVOC) | $mg/(m^2 \cdot h)$ | 1 | 0.140 | Guideline for indoor air quality testing (Notification 2010-24 of the Ministry of Environment) |
| Toluene | $mg/(m^2 \cdot h)$ | 1 | ND | Guideline for indoor air quality testing (Notification 2010-24 of the Ministry of Environment) |
| Formaldehyde | $mg/(m^2 \cdot h)$ | 1 | 0.002 | Guideline for indoor air quality testing (Notification 2010-24 of the Ministry of Environment) |

※ ND – Not Detected

--- See the attached pages ---

| Confirmation | Drafts man Name | Kim Hyeon-Jin | Technical director Name | Yoo Kyoung-Whan |
|---|---|---|---|---|

Note: 1. This test report is a result of testing with specimens wherein the specimens and the specimen names have been provided by the client, and it does not guarantee the quality of all the products.
2. This test report may not be used for promotion, propaganda, advertisement or litigation, and is prohibited to be used for any purpose other than the agreed upon use.

President of Korea Conformity Laboratories (Sealed)

Head laboratory : Gasan-dong 459-28, Geumcheon-gu, Seoul, 153-803 Korea
Contact the results : Safety & environment center (Hyundai I-Valley 805, Dang-dong 14-1, Gunpo-city, Gyeonggi-do, Korea) Tel: 031-389-9184

FIG. 3A

TEST REPORT

Test report No. : ESR2730031

Attached data

1. Test conditions in small chamber

| Sample type | Liquid building materail | Sample classification | Putty |
|---|---|---|---|
| Coating thickness | 2.0 mm | Curing time | 3 hours |
| Temperature | 24.7 °C ~ 25.3 °C | Sample load rate | $0.4 m^2/m^3$ |
| Relative humidity | 47 % ~ 53 % | Number of ventilation | 0.50 times/h |

- Test period : Seven days (chamber)

2. Analysis condition on total volatile organic compounds (TVOCs) and VOC

| Thermal Desorber: TurboMatrix ATD (PERKIN-ELMER) | | | | | |
|---|---|---|---|---|---|
| | Sampling tube | Internal trap | | Valve | Transterine |
| | | Conc. | Desorp. | | |
| Temperature (°C) | 295 | -30 | 300 | 250 | 280 |
| Timing (min) | 10 | | 2 | - | - |
| Carrier gas | He. 1.2mL/min | | | | |
| Gas Chromatograph/Mass Spectrometer : GCMS-OP2010 (SHIMADZU) | | | | | |
| Column | DB-1 (60 m × 0.32 mm × 1.0 µm film thickness) | | | | |
| Temp.program | 35 °C (5 min) → 6°C/min → 280°C (10min) | | | | |
| MS ionization mode | EI (Electron Ionization, 70eV) | | | | |
| Detection mode | Scan. m/z 35 ~ 350 | | | | |

3. Analysis condition on formaldehyde

| HPLC : LC-10Avp (SHIMADZU) | |
|---|---|
| Column | C18 (150 mm × 2.3 mm × 2.0 µm particle size) |
| Column temperature | 40 °C |
| Injection volume | 5 µL |
| Flow rate | 0.4 mL/min |
| Mobile phase | Acetonitrile/Water : 30/70 → 90/10 |
| Analysis time | 20 min |

TEST REPORT

1. Test report No. : ESR2730029
2. Client
   ○ Company name : B&G Communication Co., Ltd.
   ○ Address : 45-1010 (Seocho Eovill, Seocho-dong), Hyoryeong road 53, Seocho-gu, Seoul, Korea
   ○ Referral date : July 30, 2012
   ○ Test report issue date : November 26, 2012
3. Use of the test report : Quality control
4. Sample name : Functional paint
5. Test results

| Test item | Unit | Class | Test result | Test method |
|---|---|---|---|---|
| Formaldehyde adsorption rate of first day | % | 1 | 66.3 | Suggested by client (ISO 1600-23 : 2009) |
| Formaldehyde adsorption rate of third day | % | 1 | 62.9 | Suggested by client (ISO 1600-23 : 2009) |
| Formaldehyde adsorption rate of fifth day | % | 1 | 63.3 | Suggested by client (ISO 1600-23 : 2009) |
| Formaldehyde adsorption rate of seventh day | % | 1 | 59.3 | Suggested by client (ISO 1600-23 : 2009) |
| Accumulated adsorption amount | $\mu g/m^2$ | 1 | 5.901 | Suggested by client (ISO 1600-23 : 2009) |
| Re-radiation rate | $Mg/(m^2 \cdot h)$ | 1 | 0.008 | KS I ISO 16000-9 : 2004 |

※ adsorption rate (%) = (Supply concentration – Outlet concentration ) / Supply concentration × 100
※ Re-radiation : 1 day --- See the attached pages ---

| Confirmation | Drafts man Name | Kim Hyeon-Jin | Technical director Name | Yoo Kyoung-Whan |
|---|---|---|---|---|

Note: 1. This test report is a result of testing with specimens wherein the specimens and the specimen names have been provided by the client, and it does not guarantee the quality of all the products.
2. This test report may not be used for promotion, propaganda, advertisement or litigation, and is prohibited to be used for any purpose other than the agreed upon use.

President of Korea Conformity Laboratories (Sealed)

Head laboratory : Gasan-dong 459-28, Geumcheon-gu, Seoul, 153-803 Korea
Contact the results : Safety & environment center (Hyundai I-Valley 805, Dang-dong 14-1, Gunpo-city, Gyeonggi-do, Korea) Tel: 031-389-9184

FIG. 4A

TEST REPORT

Test report No. : ESR2730029

※ Test Condition
1. Test conditions in adsorption test chamber

| Temperature | 24.4 ℃ ~ 25.6 ℃ | Number of ventilation | 0.50 /h |
|---|---|---|---|
| Relative humidity | 48 % R.H. ~ 52% R.H. | Sample load rate | 2.0 m²/m³ |
| Supply air concentration | 217.7μg/m³ – 229.8 μg/m³ | Test period | 7 days |

2. Analysis condition on formaldehyde

| Elution | Acetonitrile, 5 mL |
|---|---|
| Detector | UV/VIS 360 nm |
| Column | C₁₈(150 mm Length × 2.0 mm inner diameter × 2.2 mm particle size) |
| Mobile Phase | Acetonitrile/Water(30/70 v/v → 90/0 v/v) |
| Analysis Time | 17 min |
| Injection Volume | 5 μL (Autoinjector) |
| Column Temperature | 40 ℃ |
| Flow Rate | 0.4 mL/min |

TEST REPORT

1. Test report No. : ESR1200174
2. Client
   - Company name : B&G Communication Co., Ltd.
   - Address : 45-1010 (Seocho Eovill, Seocho-dong), Hyoryeong road 53, Seocho-gu, Seoul, Korea
   - Referral date : July 30, 2012
   - Test report issue date : November 23, 2012
3. Use of the test report : Quality control
4. Sample name : Functional paint
5. Test results

| Test item | Unit | Class | Test result | Test method |
|---|---|---|---|---|
| Moisture adsorption and desorption | g/m$^2$ | 71.5 | ISO 24353 : 2008 | - Temperature (Min: 22.6℃, Max:25.1℃) - Humidify (Min: 27%, Max:35% R.H.) |
| Moisture desorption | g/m$^2$ | 53.3 | ISO 24353 : 2008 | |
| Difference between moisture adsorption and desorption | g/m$^2$ | 18.2 | ISO 24353 : 2008 | |

※ Mean of moisture adsorption and desorption: 62.4 g/m$^2$

--- See the attached pages ---

| Confirmation | Drafts man Name | Kim Hyeon-Jin | Technical director Name | Yoo Kyoung-Whan |
|---|---|---|---|---|

Note: 1. This test report is a result of testing with specimens wherein the specimens and the specimen names have been provided by the client, and it does not guarantee the quality of all the products.
2. This test report may not be used for promotion, propaganda, advertisement or litigation, and is prohibited to be used for any purpose other than the agreed upon use.

President of Korea Conformity Laboratories (Sealed)

Head laboratory : Gasan-dong 459-28, Geumcheon-gu, Seoul, 153-803 Korea
Contact the results : Safety & environment center (Hyundai I-Valley 805, Dang-dong 14-1, Gunpo-city, Gyeonggi-do, Korea) Tel: 031-389-9184

TEST REPORT

Test report No. : ESR1200174

Attached data

3. Test conditions

| Temperature condition | Humidity condition (Relative humidity %) | | | |
|---|---|---|---|---|
| (23 ± 0.5) ℃ | Medium moisture area | Curing process | moisture adsorption process | moisture desorption process |
| | | | 1 step | 2 steps |
| | 1 Cycle | (50 ± 1) % | (75 ± 1) % | (50 ± 1) % |
| | | | 12 | 12 |

4. Calculations and results

| Moisture adsorption | | Change in amount of moisture at the end of moisture adsorption process (g/m²) | 71.5 |
|---|---|---|---|
| Moisture desorption | | Change in amount of moisture at the end of moisture desorption process (g/m²) | 53.3 |
| Difference between moisture adsorption and desorption | | Difference between moisture adsorption and desorption at the end of test (g/m²) | 18.2 |
| Moisture adsorption and desorption rates | | Moisture adsorption and desorption rates at n time g/(m²·h) | |

$m_a$ : Mass of specimen at the end of moisture adsorption process (g)
$m_d$ : Mass of specimen at the end of moisture desorption process (g)
$m_c$ : Mass of specimen at the end of curing process (g)
A : Surface area of moisture adsorption and desorption (m²)
$m_n$ : Mass of specimen at n time
$m_{n-1}$ : Mass of specimen at n-1 time
Δt : Elapsed time

TEST REPORT
Test report No. : ESR1200174
Attached data
5. Graph of moisture adsorption and desorption
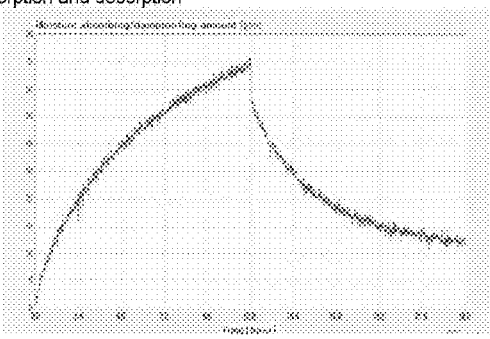
6. Graph of moisture adsorption and desorption rates
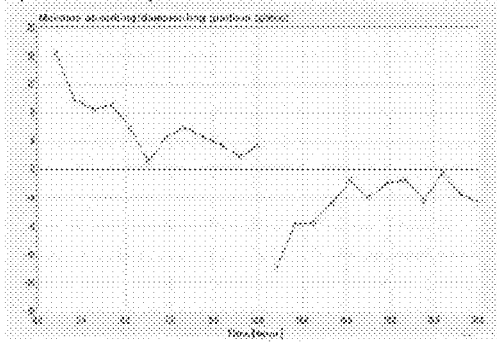
---- See the attached pages ----
4/4
FIG. 5C 1. Test report No. : ESR2730032
2. Client
   ○ Company name : B&G Communication Co., Ltd., Kim Dong-ju
   ○ Address : 45-1010 (Seocho Eovill, Seocho-dong), Hyoryeong road 53, Seocho-gu, Seoul, Korea
   ○ Referral date : July 30, 2012
   ○ Test report issue date : December 04, 2012
3. Use of the test report : Quality control
4. Sample name : functional paint
5. Test results

| Test item | Unit | Class | Test result | Test method |
|---|---|---|---|---|
| low-temperature stability | - | 1 | Test OK | KS F 4715 : 2007 |
| resistance to tiny cracking according to initial drying | - | 1 | Test OK | KS F 4715 : 2007 |
| adhesion strength-standard | N/mm$^2$ | 1 | 0.9 | KS F 4715 : 2007 |
| resistance to repeated warm and cool operations-appearance | - | 1 | Test OK | KS F 4715 : 2007 |
| resistance to repeated warm and cool operations-adhesion | N/mm$^2$ | 1 | 0.7 | KS F 4715 : 2007 |
| water absorption coefficient (W) | Kg/(m$^2$·h$^{0.5}$) | 1 | 0.12 | KS F 4715 : 2007 |
| resistance to washing | - | 1 | Test OK | KS F 4715 : 2007 |
| resistance to impact | - | 1 | Test OK | KS F 4715 : 2007 |
| resistance to alkali | - | 1 | Test OK | KS F 4715 : 2007 |
| resistance to discoloration/fading-discoloration | | 1 | 4-5 | KS F 4715 : 2007 |
| moisture permeability (sd) | m | 1 | 1.3 | KS F 4715 : 2007 |

--- See the attached pages ---

| Confirmation | Drafts man Name | Yoon Chang-su | Technical director Name | Kim Shang-Chul |
|---|---|---|---|---|

Note: 1. This test report is a result of testing with specimens wherein the specimens and the specimen names have been provided by the client, and it does not guarantee the quality of all the products.
2. This test report may not be used for promotion, propaganda, advertisement or litigation, and is prohibited to be used for any purpose other than the agreed upon use.

President of Korea Conformity Laboratories (Sealed)

FIG. 6

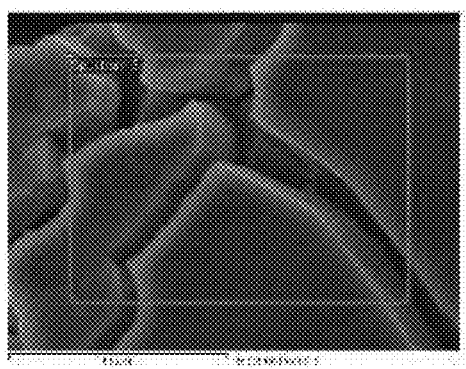 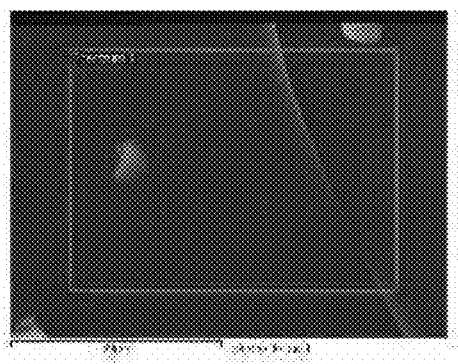
FIG. 7A
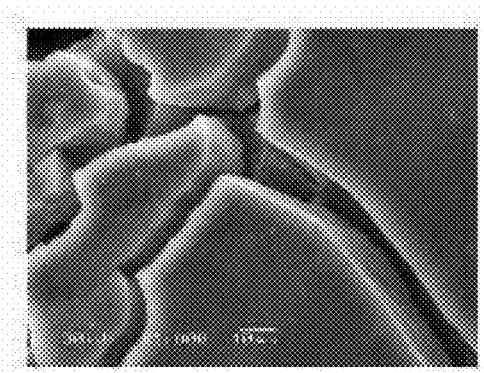 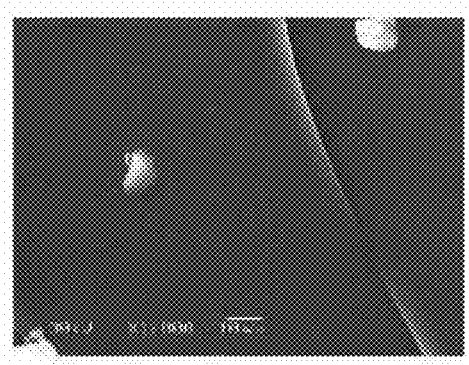
FIG. 7B
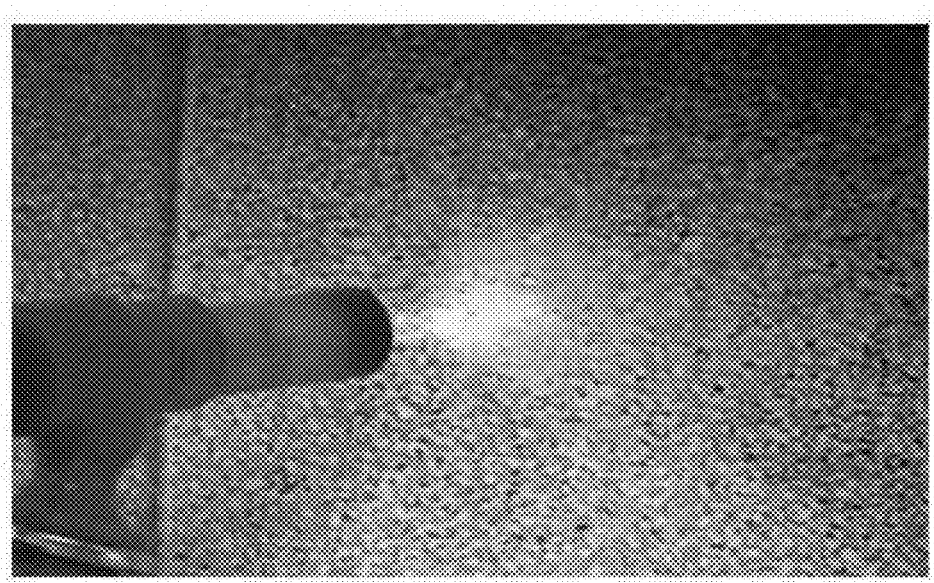
FIG. 8 ific to an eco-friendly water-based paint composition for interior finishing materials of buildings, and more specifically to an eco-friendly water-based paint composition for interior finishing materials of buildings, which can be used by painting on a cement surface forming the inner wall surface of a cement building, can neutralize and absorb the toxicity of cement, can perform an indoor humidity adjusting function, and can perform anti-microbial, anti-fungal, deodorization and offensive odor removal functions.

ECO-FRIENDLY WATER-BASED PAINT COMPOSITION FOR INTERIOR FINISHING MATERIALS OF BUILDINGS

BACKGROUND OF THE INVENTION

1. Field of the Invention

The present invention relates to an eco-friendly water-based paint composition for interior finishing materials of buildings, and more specifically to an eco-friendly water-based paint composition for interior finishing materials of buildings, which can be used by painting on a cement surface forming the inner wall surface of a cement building, can neutralize and absorb the toxicity of cement, can perform an indoor humidity adjusting function, and can perform anti-microbial, anti-fungal, deodorization and offensive odor removal functions.

2. Description of the Related Art

Nowadays most buildings that are constructed can be said to be cement structures with a steel frame as the basis. A cement structure refers to a building which includes a steel-frame structure and uses cement as a raw material for the main material of an interior and exterior finish. The most important point in such a building lies in securing as much indoor space as possible. A cement building basically uses flowable cement mortar and has various external structures and different indoor spaces according to the use of the building. Cement mortar can be used flexibly to construct various structures or shapes of such a building and is evaluated as one of the building finishing materials being used the most.

As is well known, building finishing materials refer to interior and exterior finishing materials of buildings. The building finishing materials refer to construction materials that are attached to the inner wall, floor surface and outer wall of buildings based on a cement wall surface to perform additional functions such as aesthetic appearance, heat insulation and waterproofing, such that the building finishing materials can be regarded as indispensable construction materials.

The building finishing materials are commonly used by being adhered by means of building adhesives, and such adhesives are widely used in daily life or in many fields of industrial activity. However, because most of the solvents of adhesives contain volatile organic substances hazardous to health, use thereof has tended to gradually decrease.

Meanwhile, as the most basic finishing material of buildings, cement mortar can be used or a cement wall surface in the form of a cement structure can be presented as an example. Such a cement wall surface has various finishing materials added thereon to form the interior. During the initial construction, various harmful components generated from the inside of cement are emitted indoors, and as a predetermined time elapses, a degradation phenomenon can occur gradually from the cement itself.

Recently, such a building has been related to the problem of new house syndrome, which has been growing in concern among the general public. As causative agents of new house syndrome, formaldehyde and volatile organic compounds (VOCs) such as toluene, xylene or the like can be mentioned. Such formaldehyde and volatile organic compounds are derived from construction materials and various finishing materials which are being used commonly nowadays. On moving into a new house, one may experience the symptoms of new house syndrome in the form of headaches and respiratory diseases caused by various organic compounds. To control such a phenomenon, the Korean government has legislated the "Indoor Air Quality Control Act."

In addition, various buildings of today have heat insulation and air-tightness reinforced to save energy, and this has led to a problem related to contamination of indoor air. As for the contamination of the indoor air, there is a need to mention the effects of formaldehyde or various organic compounds derived from interior finishing material of buildings. Such effects cause, for example, sick house syndrome or a disease known as compound hypersensitiveness, and accordingly, diseases caused by indoor air contamination are becoming a big social issue.

Such a phenomenon has been evaluated to involve a fundamental problem that cannot be avoided any longer, and will continue as long as various buildings of today use cement mortar as a finishing material or building finishing materials such as oil-based paint containing various organic compounds are used.

PRIOR ART DOCUMENT

Patent Document

Patent Document 1 Korean Patent Registration No. 10-1044966 entitled "Biotite containing composition for finishing materials of buildings" (2011 Jun. 22)

Patent Document 2 Korean Patent Registration No. 10-701632 entitled "Composition for finishing materials of buildings and finishing materials including the composition" (2007 Mar. 23)

Patent Document 3 Korean Patent Registration No. 10-1009155 entitled "Eco-friendly adhering composition for finishing materials of buildings" (2011 Jan. 11)

Patent Document 4 Korean Patent Registration No. 10-362884 entitled "Antimicrobial composition for interior finishing materials of buildings" (2002 Nov. 15)

Patent Document 5 Korean Patent Laid-open Publication No. 2005-38358 entitled "Composition for interior finishing materials of buildings" (2005 Apr. 27)

Patent Document 6 Korean Patent Laid-open Publication No. 2005-111443 entitled "Functional indoor finishing material of buildings" (2005 Nov. 25)

Patent Document 7 Korean Patent Laid-open Publication No. 2012-111090 entitled "Functional indoor finishing material of buildings using slag" (2012 Oct. 10)

SUMMARY OF THE INVENTION

In consideration of the above-mentioned circumstances, it is an object of the present invention to provide an eco-friendly water-based paint composition for interior finishing materials of buildings, which can be used by painting on the indoor wall surface of a cement building, can neutralize and absorb the toxicity of cement, can perform the indoor humidity adjusting function, and can perform the anti-microbial, anti-fungal, deodorization and offensive odor removal functions.

In order to achieve the above objects, there is provided an eco-friendly water-based paint composition for interior finishing materials of buildings including: 3 to 6 by weight ('wt. %') of diatomite for adsorbing harmful materials; 7 to 12 wt. % of titanium dioxide for enhancing a deodorization effect; 0.4 to 1.5 wt. % of antimicrobial agent-containing microcapsules for killing harmful microorganisms derived from an indoor air; 30 to 40 wt. % of an inorganic binder for binding different ingredients of the water-based paint composition so as to form a smooth surface; 3 to 10 wt. % of water for blending different materials for the water-based paint and controlling workability; and silica as the balance of a total weight of the composition, wherein the silica is a base material of the water-based paint and forms a thickness of a coating layer during working.

When manufacturing the eco-friendly water-based paint composition for interior finishing materials of buildings, the present invention can be used by simultaneously introducing in a small amount of thickener for enhancing viscosity, a small amount of defoamer for removing foam during the mixing of materials, and a small amount of dispersing agent for uniformly mixing during the mixing of raw materials and improving formability.

When the eco-friendly water-based paint composition according to the present invention is used on the wall surface of buildings, it is possible to halt the breeding of harmful germs from indoor air and the breeding of fungi also from indoor air.

In addition, when the eco-friendly water-based paint composition according to the present invention is used on the wall surface of buildings, it is possible to adsorb so as to remove formaldehyde components and organic volatile components that cause new house syndrome.

Further, when the eco-friendly water-based paint composition according to the present invention is used on the wall surface of buildings, it is possible to display an indoor air purification effect and indoor air humidity adjusting abilities.

Further, when the eco-friendly water-based paint composition according to the present invention is used on the wall surface of buildings, it is possible to attain an effect of coating an incombustible material on the outer wall of buildings.

BRIEF DESCRIPTION OF THE DRAWINGS

The above and other objects, features and other advantages of the present invention will be more clearly understood from the following detailed description taken in conjunction with the accompanying drawings, in which:

FIG. 1A to FIG. 1C are test reports that record and summarize the overall situation on antimicrobial activity experiments;

FIG. 2A and FIG. 2B are test reports that record and summarize the overall situation on antifungal activity experiments;

FIG. 3A and FIG. 3B are test reports on purification performance of an indoor air;

FIG. 4A and FIG. 4B are test reports on adsorption and removal performance of harmful volatile substances in indoor air;

FIG. 5A to FIG. 5C are test reports on humidity adjusting abilities of the indoor air;

FIG. 6 is a test report on basic painting properties of coating materials for an indoor thin wall;

FIG. 7A and FIG. 7B are electron micrographs illustrating surface effects of the water-based paint composition; and FIG. 8 is photographic data illustrating the flame retardant or non-flammable testing of the water-based paint composition.

DETAILED DESCRIPTION OF THE INVENTION

Figure 1B:
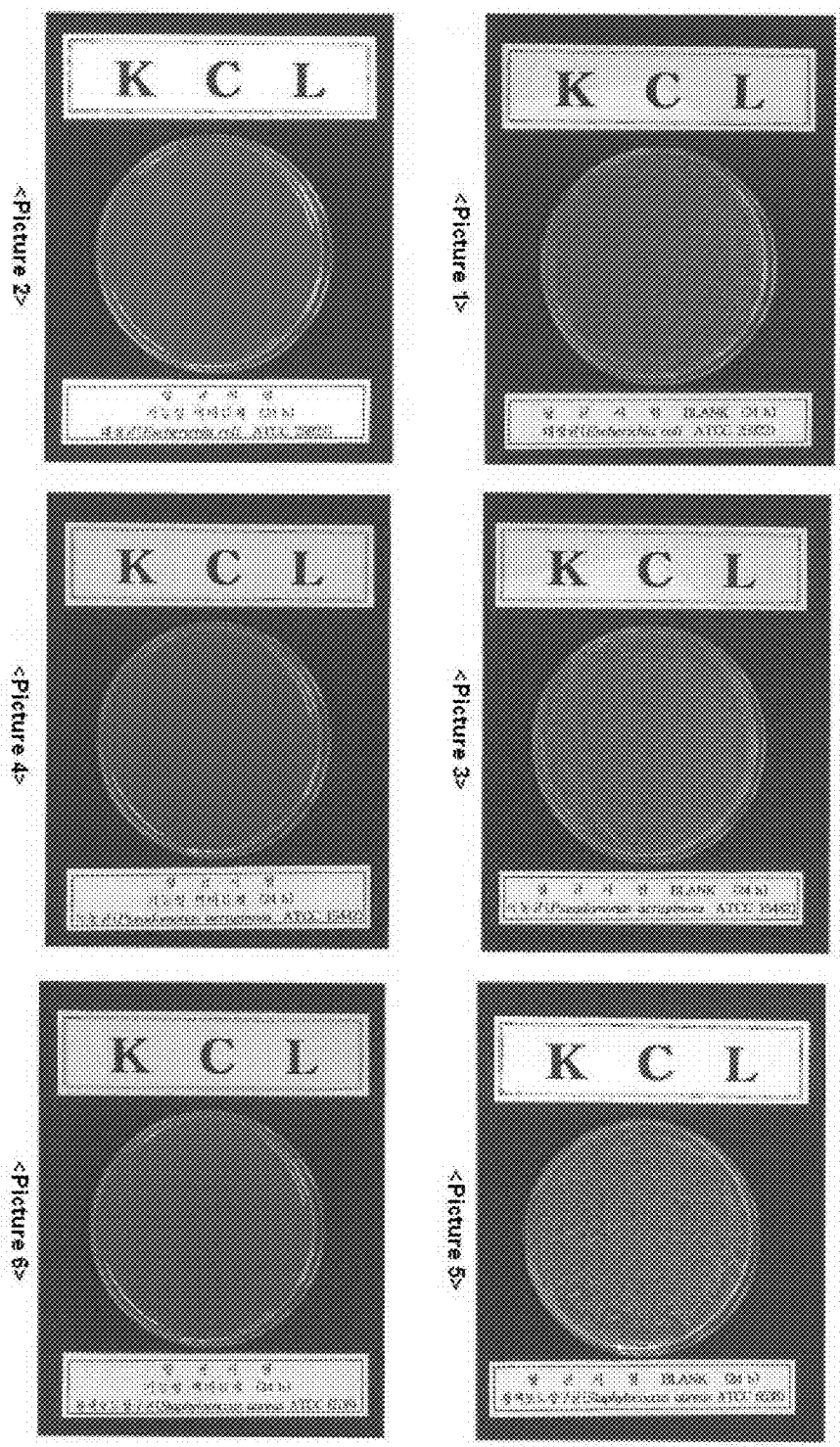

Hereinafter, preferred embodiments will be described to more concretely understand the present invention with reference to examples and comparative examples. However, those skilled in the art will appreciate that such embodiments are provided for illustrative purposes and do not limit subject matters to be protected as disclosed in the detailed description and appended claims. Therefore, it will be apparent to those skilled in the art that various alterations and modifications of the embodiments are possible within the scope and spirit of the present invention and duly included within the range as defined by the appended claims.

The present invention provides an eco-friendly water-based paint composition used on the indoor wall surface of buildings. Since the present invention relates to a water-based paint composition unlike an oil-based paint, the components thereof do not require organic solvent and do not contain volatile organic solvent harmful to the human body.

The eco-friendly water-based paint composition according to the present invention for an indoor finishing material of buildings has components carefully selected from basically inorganic materials so as to perform various functions simultaneously.

The eco-friendly water-based paint composition according to the present invention is characterized by including: 3 to 6 wt. % of diatomite for adsorbing harmful materials; 7 to 12 wt. % of titanium dioxide for enhancing a deodorization effect; 0.4 to 1.5 wt. % of antimicrobial agent-containing microcapsules for killing harmful microorganisms derived from an indoor air; 0.1 to 0.5 wt % of preservative for suppressing and preventing propagation of fungi derived from indoor air; 30 to 40 wt. % of an inorganic binder for binding different ingredients of the water-based paint composition so as to form a smooth surface; 3 to 10 wt. % of water for blending different materials for the water-based paint and controlling workability; and silica as the balance of a total weight of the composition, wherein the silica is a base material of the water-based paint and forms a thickness of a coating layer during working.

The eco-friendly water-based paint composition for interior finishing materials of buildings according to the present invention may include a diatomite component in order to adsorb harmful substances in indoor air.

According to the present invention, the diatomite is chemically inactive and does not include any harmful substance, and the diatomite in the form of natural material without calcinations is preferably used. The diatomite may include debris of diatom as a major component and an additional porous material having a size of several tens of microns wherein clay, volcanic ash, organic matter, or the like are mixed. Therefore, the diatomite is known to be applied widely to adsorbents, filtering agents, lagging materials, abrasive materials, or the like.

According to the present invention, a reason why diatomite is used in-situ as a natural material without calcinations may be considered to be so as to utilize the micro-pores already existing in the diatomite as they are. The diatomite is preferably pulverized into micro-particles having a size of about 300 to 400 mesh for use. If it is pulverized too much out of the above range, there may be difficulties in utilizing the micro-pores of the diatomite. When it is too coarse, the diatomite is not preferably used as a finishing material of buildings. Further, the diatomite is preferably used in an amount of 3 to 6% wt. % to the total weight of the composition. If the foregoing amount is less than 3 wt. % to the total weight of the composition, performance for adsorption of a harmful substance is deteriorated. On the other hand, if the foregoing amount is 6 wt. % or more to the total weight of the composition, performance for adsorption of a harmful substance is not further improved in proportion to an introduced amount of the diatomite.

The eco-friendly water-based paint composition for interior finishing materials of buildings according to the present invention may include 7 to 12 wt. % of a titanium dioxide component to the total weight of the composition, in order to improve deodorizing effects.

According to the present invention, titanium dioxide $TiO_2$ is well known as a photocatalyst and may be classified into anatase type and rutile type substances. According to the present invention, the anatase type substance is preferably used. A reason of the foregoing fact is because the anatase type is more biologically or chemically stable than the rutile type. Titanium dioxide (hereinafter, referred to '$TiO_2$') may be used to degrade and remove harmful substances from indoor air, and enhance a quality of indoor air. If the amount of the $TiO_2$ component is 7 wt. % or less relative to the total weight of the composition, it cannot effectively achieve adequate air purification of indoor air. If the amount of the $TiO_2$ component is 12 wt. % or more relative to the total weight of the composition, indoor air is not further purified in proportion to the foregoing introduced amount, therefore, the foregoing amount is not preferable.

The eco-friendly water-based paint composition for interior finishing materials of buildings according to the present invention may include 0.4 to 1.5 wt. % of an antimicrobial agent-containing microcapsules to the total weight of the composition, wherein each microcapsule kills harmful microorganisms derived from indoor air.

According to the present invention, the antimicrobial agent-containing microcapsule includes an antimicrobial component inside a barrier wall of a micro-spherical form, and has a configuration in that, when giving an external impact thereto, the barrier wall of a micro-spherical form is collapsed and the antimicrobial component contained in the barrier wall is released to the outside. The microcapsule is provided for protecting the antimicrobial component sealed therein against external contamination and from becoming damaged until the antimicrobial component is needed to be taken out of the microcapsule and used, or for isolating the foregoing component so as not to react with other substances. The spherical barrier wall of the microcapsule is configured to be broken by an external impact applied thereto.

According to the present invention, the antimicrobial agent-containing microcapsule is more preferably configured such that the antimicrobial component sealed therein is slowly released to the outside over time. With such a configuration as described above, it may be accomplished that the antimicrobial component is released as soon as the water-based paint of the present invention is spread or applied to an inner wall surface of buildings and, even after quite some time has passed, the antimicrobial component is continuously released from the surface of the water-based paint over time, so as to protect occupants from harmful microorganisms inside the building.

For the foregoing purposes, a micro-spherical barrier wall of the microcapsule is preferably made of an alkaline material. When the spherical barrier wall of the microcapsule is formed using an alkaline material, a diatomite component among different ingredients of the water-based paint may adsorb carbon dioxide ($CO_2$) in indoor air over time. Herein, when such $CO_2$ having chemically subacid properties contacts with a spherical barrier wall, which is made of an alkaline material, filled with the antimicrobial agent and sealed, the above gas may collapse the spherical barrier wall made of an alkaline material, thus enabling the antimicrobial agent sealed therein to be released to the outside. In addition, as time passes, a cement wall surface of buildings is gradually degraded and shows a tendency of neutralization during the degradation. During neutralizing, the spherical barrier wall of the microcapsule is also collapsed and the antimicrobial component sealed therein may be slowly released to the outside.

According to the present invention, when the antimicrobial agent-containing microcapsule is included in an amount of 0.4 wt. % or less to the total weight of the composition, it is difficult to prevent propagation of harmful microorganisms derived from indoor air. On the other hand, when the antimicrobial agent-containing microcapsule is included in an amount of 1.5 wt. % or more to the total weight of the composition, it does not have economic advantages, thus not being preferable. Meanwhile, the antimicrobial agent described herein may be any conventional antimicrobial agent filled in a sealed microcapsule to be used, therefore, a detailed description thereof will be omitted.

The eco-friendly water-based paint composition for interior finishing materials of buildings according to the present invention may include a preservative in an amount of 0.1 to 0.5 wt. % to the total weight of the composition, wherein the preservative may suppress and/or prevent propagation of fungi derived from indoor air.

According to the present invention, such fungi may mean a mold and, when the indoor air is moist at a high temperature, the inventive composition may function to inhibit and eliminate propagation of various molds generated on a wall surface or an inner floor. According to the present invention, inhibition and prevention of molds may be executed by any conventional method or process, and therefore, a detailed description thereof will be omitted.

The eco-friendly water-based paint composition for interior finishing materials of buildings according to the present invention may include an inorganic binder in an amount of 30 to 40 wt. % to the total weight of the composition, wherein the inorganic binder causes a surface to become smooth after applying the water-based paint thereto.

According to the present invention, the inorganic binder may simultaneously perform at least three functions, as described below.

According to the present invention, the inorganic binder may primarily function to bind different ingredients of the water-based paint composition to one another. The inorganic binder used herein may be an inorganic binder solution prepared by mixing an alkaline silicate solution, which is an inorganic compound, and inorganic acid having strong acidity ('strongly acidic inorganic acid') in a ratio by weight of 1:0.5 to 2. The alkaline silicate solution is preferably a silicate solution containing potassium ions. Meanwhile, the strongly acidic inorganic acid may be any one selected from sulfuric acid ($H_2SO_4$), hydrochloric acid (HCl) and nitric acid ($HNO_3$). The inorganic binder based on such inorganic components, as described above, may be cured by applying or injecting the water-based paint to a wall surface of a building to coat the same, thus accomplishing the intended functions thereof.

According to the present invention, a principle of curing the foregoing inorganic components is as follows: when the alkaline silicate component and the inorganic acid are admixed, a potassium ion ($K^+$) is bonded to a sulfuric acid and a hydrogen ion ($H^+$) free from the sulfuric acid is combined with a hydroxyl ion ($OH^-$) to thus form a water molecule ($H_2O$), which in turn, leads to a condensation reaction. As a result, the alkaline silicate is bound with an adjacent alkaline silicate component and such a binding relation may be repeated, which in turn, forms an overall network through binding of silicon components.

According to the present invention, the inorganic binder may perform surface smoothing to keep the surface flat and smooth, after binding different ingredients of the water-based paint composition to one another. The foregoing performance may be a secondary function of the binder. The surface smoothing performance of the inorganic binder resin may include not only surface smoothing when the water-based paint is applied to a wall surface of building, but also continuously keeping the surface smooth, such as at the beginning, without a crack or distortion of the surface even after a water portion in the water-based paint is completely evaporated.

The water-based paint of the present invention may retain substantially the same surface smoothness as that at the beginning, even after the water portion is evaporated from the water-based paint over time. The foregoing result (that is, sustained surface smoothness) is based on a curing principle of the above inorganic component-based binder, as described above.

More particularly, unlike a conventional water-based paint, the water-based paint of the present invention may form an overall network through binding of silicon components by: combining a hydrogen ion ($H^+$) free from sulfuric acid with a hydroxyl ion ($OH^-$) contained in the alkaline silicate to generate a water molecule ($H_2O$), leading to a condensation reaction; therefore, enabling the alkaline silicate to be bound with an adjacent alkaline silicate component. In fact, a water portion generated during a condensation reaction is evaporated into air and never affects a binding relation in the water-based paint. In addition, further added water may also not affect the binding relation in the water-based paint of the present invention.

The conventional water-based paint has fine cracks or gaps on the surface thereof due to water evaporation. By contrast, the eco-friendly water-based paint of the present invention does not involve such conditions, thus having a considerable difference, as compared to conventional water-based paint.

According to the present invention, when the foregoing inorganic binder is used as an ingredient of the water-based paint for a wall surface of a building, it may exhibit a tertiary function of assisting non-flammable properties of the water-based paint. Binder and coupling agent ingredients in a typical paint generally include organic compounds. Such an organic compound is vulnerable to heat at a high temperature and also usually generates a toxic gas due to the heat at a high temperature. In this regard, the organic compound entails difficulties in acting as a flame retardant. On the other hand, since the present invention uses a silicate component and adopts an inorganic component as a binder, it can fully achieve it's potential, which is not achievable with organic compounds, as a non-flammable material.

According to the present invention, when the inorganic binder is used in an amount of 30 wt. % or less to the total weight of the composition, a silica component described below may be included in a relatively large and undesired amount and a content of inorganic component may be reduced, therefore, the foregoing amount is not preferable. On the other hand, when the inorganic binder is included in an amount of 40 wt. % or more to the total weight of the composition, the inorganic component may be included in relative excess, thus not being preferable.

The eco-friendly water-based paint composition for interior finishing materials of buildings according to the present invention may further include 3 to 10 wt. % of water, in order to blend different materials for the water-based paint and control workability. Water may act as a mixing agent in the water-based paint and, if the working is conducted by applying or spraying the water-based paint to a wall surface of a building, water may control workability. Water is typically added to the water-based paint in a blending process and a detailed description thereof will be omitted.

The eco-friendly water-based paint composition for interior finishing materials of buildings according to the present invention may further include silica as the balance of the total weight of the composition, wherein the silica is a base material of the water-based paint and forms a thickness of a coating layer during working.

According to the present invention, a content of silica may be the balance of a total 100 wt. % after adding up different ingredients of the water-based paint. In general, although the content of silica may range from about 30 wt. % to about 70 wt. %, a specific content of silica may depend upon a mixing ratio of different ingredients of the water-based paint. In addition, the silica used herein is preferably pulverized into micro-particles in a range of about 300 to 400 mesh. It is substantially needless to excessively pulverize the silica out of the foregoing range. If it is too coarse, the silica may not be preferred as a finishing material for a building. According to the present invention, the silica is also an inorganic material and may be used for forming a thickness of the water-based paint according to the present invention.

Furthermore, the silica may significantly contribute to providing non-flammability to a building where the water-based paint of the present invention is applied to a wall surface of the building. The reason for this fact is because the silica, combined with the silicate component described above, is an inorganic material thus providing non-flammable properties and a component including the highest composition ratio in the water-based paint. Consequently, it is understood that the silica may have a primary function as a base material of the water-based paint according to the present invention and, at the same time, a secondary function to provide non-flammable properties to the water-based paint according to the present invention.

Hereinafter, particular examples of the eco-friendly water-based paint composition according to the present invention and experimental results thereof will be described in more detail.

Preparative Example 1

To 31 kg of an inorganic binder solution including 15 kg of an alkaline silicate solution and 16 kg of sulfuric acid, 45 kg of 300 mesh silica and 4 kg of 320 mesh diatomite were introduced. After adding 7 kg of water thereto, the solution was slowly agitated. Next, 10 kg of titanium dioxide and 1.1 kg of an antimicrobial agent in a microcapsule form were further introduced thereto, followed by slowly agitating, to yield 98.1 kg of a homogeneous water-based paint composition. The water-based paint composition was in a diluted mortar form.

Preparative Example 2

The same procedures as described in Preparative Example 1 were conducted except that 0.2 kg of a preservative was additionally introduced. The obtained water-based paint composition was also in a diluted mortar form.

Antimicrobial Activity Experiments 1 to 3

In order to identify antimicrobial activity of the water-based paint composition obtained in Preparative Example 1, Korea Conformity Laboratories ('KCL', which is established by the Korea construction, environment & merchandise testing institute, Gasan-dong 459-28, Geumcheon-gu, Seoul, Korea) was requested to execute an antimicrobial test. KCL selected *Escherichia coli* ATCC 25922, *Pseudomonas aeruginosa* ATCC 15442 and *Staphylococcus aureus* ATCC 6538, as test strains, and executed an antimicrobial test with these strains by its own test method (KCL-FIR-1002:2011).

It was demonstrated that these strains showed a decrease in bacteria of 99.9% or higher, compared to initial concentrations thereof.

FIG. 1A illustrates a cover of a test report on the antimicrobial activity experiments, FIG. 1B illustrates the experimenting of antimicrobial activity using the *Escherichia coli, Pseudomonas aeruginosa* and *Staphylococcus aureus*, and control groups thereof respectively, and FIG. 1C illustrates the final results on antimicrobial activity experiments in the form of a test report.

Antifungal Activity Experiment

In order to identify antifungal activity of the water-based paint composition obtained in Preparative Example 2, KCL was requested to execute an antifungal test. KCL selected a mixed fungi strain of *Aspergillus niger* ATCC 9642, *Penicillium pinophilum* ATCC 11797, *Chaetomium globosum* ATCC 6205, *Gliocladium virens* ATCC 9645, and *Aureobasidium pullulans* ATCC 15233, as the test strains, and executed an antifungal test with these strains by a test method of ASTM G 21: 2009

Results of the above experiment have demonstrated that the fungi rarely exhibited growth ranging from one week to four weeks.

FIG. 2A is a cover of a test report on the experiments using the mixed fungi strains, and FIG. 2B illustrates proceeding of the antifungal activity experiments using the mixed fungi strains.

Absorption Performance Experiment 1 of Volatile Organic Compounds

In order to identify an ability of purifying indoor air through absorption of volatile organic compounds contained in indoor air using the eco-friendly water-based paint composition obtained in Preparative Example 1, KCL was requested to execute an absorption test of volatile organic compounds, so as to determine performance for absorption of the volatile organic compounds. KCL adopted total volatile organic compounds (TVOC), toluene and formaldehyde, as test items, and executed an experiment for purification of indoor air in regard to the foregoing items according to guidelines for indoor air quality testing (Notification 2010-24 of the Ministry of Environment).

Results of the above experiment demonstrated that TVOC was 0.140 mg/(m$^2$·h), toluene was not detected, and formaldehyde was only 0.002 mg/(m$^2$·h).

FIG. 3A is a cover of a test report on purification performance of indoor air, and FIG. 3B illustrates the test report on purification performance of indoor air.

Absorption Performance Experiment 2 of Volatile Organic Compounds

In order to identify an ability of purifying indoor air through absorption of formaldehyde contained in indoor air using the eco-friendly water-based paint composition obtained in Preparative Example 2, KCL was requested to execute an absorption test of formaldehyde, so as to determine performance for absorption thereof. KCL adopted formaldehyde as test items, and executed an experiment for purification of indoor air in regard to the foregoing items according to an 'ISO 16000-23: 2009' method as the testing method to determine adsorption rates thereof after passing one day, three days, five days, and seven days.

Results of the above experiment have demonstrated that the adsorption rate of the first day is 66.3%, the adsorption rate of the third day is 62.9%, the adsorption rate of the fifth day is 63.3%, and the adsorption rate of seventh day is 59.3%, respectively.

FIG. 4A is a cover of a test report showing the experiment results of an absorption test of formaldehyde, and FIG. 4B illustrates experiment conditions of the absorption test of formaldehyde.

Humidity Control Performance Experiment of Indoor Air

In order to identify how much a humidity of the indoor air can be controlled when an inner wall surface was finished using the eco-friendly water-based paint composition obtained in Preparative Example 1, KCL was requested to execute an experiment to determine humidity control performance. KCL selected moisture adsorption and desorption, as test items, and executed an experiment for humidity control performance in indoor air, in regard to the foregoing items, according to an 'ISO 24353:2008' method.

Results of the above experiment demonstrated that the moisture absorption and moisture desorption at an indoor temperature of 23±0.5° C. were 71.5 g/m$^2$ and 53.3 g/m$^2$, respectively, therefore, a difference between the moisture absorption and moisture desorption was 18.2 g/m$^2$.

FIG. 5A is a cover of a test report on humidity adjusting abilities of indoor air, FIG. 5B illustrates experiment conditions of the humidity adjusting abilities of the indoor air and result data thereof, and FIG. 5C illustrates a graph on the humidity adjusting abilities of the indoor air.

Basic Physical Property Experiment of Coating Materials for an Indoor Thin Wall

In order to identify as to whether the coating materials for an indoor thin wall can be used when an inner wall surface was finished using the eco-friendly water-based paint composition obtained in Preparative Example 1, KCL was requested to execute an experiment to determine basic physical properties thereof. KCL has selected low-temperature stability, resistance to tiny cracking according to initial drying, adhesion strength, resistance to repeated warming and cooling operations, water absorption coefficient, resistance to washing, resistance to impact, resistance to alkali, resistance to discoloration/fading, moisture permeability, and the like as test items, and executed an experiment to determine basic physical properties as an indoor paint, in regard to the foregoing items, according to a 'KSF 4715: 2007' method.

Results of the above experiment have demonstrated that the eco-friendly water-based paint composition according to the present invention has sufficient physical properties as the indoor paint.

FIG. 6 is a copy of a test report showing test items, test results, and the like according to the 'KSF 4715: 2007' method.

Surface Smoothness Experiment (1)

In order to identify cracks and/or fine debris formed on a surface of buildings when the water-based paint composition obtained in Preparative Example 1 was applied to the surface of buildings, an experiment was executed according to the KSF 4715 test method.

As a result, it was demonstrated that, when using the water-based paint obtained in Preparative Example 1, the surface was smooth enough such that no crack occurred on the surface even after water evaporation.

FIG. 7A illustrates EDS analysis results of surfaces where the water-based paint composition obtained in Preparative Example 1 was used and a control including a conventional silicate product as a binder was used, respectively.

Surface Smoothness Experiment (2)

In order to identify cracks and/or fine debris formed on a surface of buildings when the water-based paint composition obtained in Preparative Example 1 was applied to the surface of buildings, an experiment was executed according to the KSF 4715 test method.

As a result, it was demonstrated that, when using the water-based paint obtained in Preparative Example 1, the surface was smooth so much and no crack has occurred on the surface even after water evaporation.

FIG. 7B illustrates SEM analysis results of surfaces where the water-based paint composition obtained in Preparative Example 1 was used and a control including a conventional silicate product as a binder was used, respectively.

Non-Flammability Experiment

In order to identify as to whether a building is poorly flame retardant or non-flammable when the water-based paint composition obtained in Preparative Example 1 was applied to a surface of the building, a high-temperature flame directly contacting the surface of the building by means of a torch was used.

As a result, it was demonstrated that almost no gas was generated when a fire source (that is, the torch flame) directly contacted with the surface of the building, and embers did not remain and were instantly extinguished when the fire source was removed from the same. It was predicted from the foregoing experimental results that, the water-based paint composition of the present invention being used as a finishing material of buildings, may exhibit the same performance as that of a non-combustible material with flame-retardant grade 1. However, it should be pointed out that, since there is still no experimental method that can be executed for the record in regard to flame-retardant grade 1 of water-based paints and/or performance test of non-combustible materials, no formal test record has been appended to the present text.

FIG. 8 illustrates directly contacting the high-temperature flame with the surface of the building by means of a torch, after the water-based paint composition obtained in Preparative Example 1 was applied to a surface thereof.

As described above, although the eco-friendly water-based paint composition for buildings and its effects using the same have been concretely described, the foregoing description is only for purpose of illustrating most preferred embodiments of the present invention, however, the scope of the present invention is not particularly limited thereto but defined and restricted by the appended claims.

Further, it will be obviously understood that those skilled in the art can conceive and/or invent various modifications and imitations on the basis of the foregoing detailed description regarding the present invention, however, these are also included within the scope of the present invention.

What is claimed is:

1. An eco-friendly water-based paint composition for interior finishing materials of buildings comprising:

3 to 6 wt. % of diatomite for adsorbing harmful materials;

7 to 12 wt. % of titanium dioxide for enhancing a deodorization effect;

0.4 to 1.5 wt. % of antimicrobial agent-containing microcapsules for killing harmful microorganisms derived from an indoor air;

30 to 40 wt. % of an inorganic binder for binding different ingredients of the water-based paint composition so as to form a smooth surface;

3 to 10 wt. % of water for blending different materials for the water-based paint and controlling workability; and silica as the balance of a total weight of the composition, wherein the silica is a base material of the water-based paint and forms a thickness of a coating layer during working.

2. The composition according to claim 1, further comprising 0.1 to 0.5 wt % of preservative to a total weight of the composition for suppressing and preventing propagation of fungi derived from indoor air.

3. The composition according to claim 1, wherein the diatomite is chemically inactive and does not include any harmful substance, and is used in the form of a natural material without calcinations.

4. The composition according to claim 1, wherein the antimicrobial agent-containing microcapsule includes an antimicrobial component inside a barrier wall of a micro-spherical form, and the micro-spherical barrier wall of the microcapsule is made of an alkaline material to adsorb carbon dioxide ($CO_2$) in indoor air over time, such that the alkaline barrier wall of the microcapsule is collapsed by the carbon dioxide ($CO_2$) so as to slowly release an antimicrobial component sealed therein to the outside for continuously providing antimicrobial performances.

5. The composition according to claim 1, wherein the inorganic binder has a primary function to bind different ingredients of the water-based paint composition to one another, a secondary function to keep the surface flat and smooth, after binding different ingredients of the water-based paint composition to one another, and a tertiary function to assist non-flammable properties when the water-based paint is used on an indoor wall surface of buildings.

6. The composition according to claim 1, wherein the inorganic binder is an inorganic binder solution prepared by mixing an alkaline silicate solution, which is an inorganic compound, and inorganic acid having strong acidity in a ratio by weight of 1:0.5 to 2.

\* \* \* \* \*